(12) United States Patent
Petruno et al.

(10) Patent No.: US 10,191,043 B2
(45) Date of Patent: Jan. 29, 2019

(54) METHODS AND SYSTEMS FOR CALIBRATING ILLUMINATION SOURCE OF DIAGNOSTIC TEST SYSTEM

(71) Applicant: Alverix, Inc., San Jose, CA (US)

(72) Inventors: Patrick T. Petruno, San Jose, CA (US); John F. Petrilla, Palo Alto, CA (US); Michael J. Brosnan, Fremont, CA (US); Rong Zhou, Sunnyvale, CA (US); Daniel B. Roitman, Menlo Park, CA (US); Bo U. Curry, Redwood City, CA (US)

(73) Assignee: Alverix, Inc., Franklin Lakes, NJ (US)

( * ) Notice: Subject to any disclaimer, the term of this patent is extended or adjusted under 35 U.S.C. 154(b) by 0 days.

(21) Appl. No.: 15/296,872

(22) Filed: Oct. 18, 2016

(65) Prior Publication Data

US 2017/0199183 A1    Jul. 13, 2017

Related U.S. Application Data

(60) Continuation of application No. 12/409,877, filed on Mar. 24, 2009, which is a division of application No.
(Continued)

(51) Int. Cl.
*G01N 33/543* (2006.01)
*G01N 21/84* (2006.01)
(Continued)

(52) U.S. Cl.
CPC ....... *G01N 33/54386* (2013.01); *G01N 21/17* (2013.01); *G01N 21/274* (2013.01);
(Continued)

(58) Field of Classification Search
CPC .......... G01N 33/54386; G01N 21/274; G01N 21/6428; G01N 21/17; G01N 33/558;
(Continued)

(56) References Cited

U.S. PATENT DOCUMENTS

| 4,849,338 A | 7/1989 | Litman et al. |
| 4,902,278 A | 2/1990 | Maget et al. |

(Continued)

FOREIGN PATENT DOCUMENTS

| CA | 2210559 | 1/1998 |
| JP | H09297832 A | 11/1997 |

(Continued)

*Primary Examiner* — Sally A Merkling
(74) *Attorney, Agent, or Firm* — Knobbe Martens Olson & Bear LLP

(57) ABSTRACT

An assay test strip includes a flow path, a sample receiving zone, a label, a detection zone that includes a region of interest, and at least one position marker. The at least one position marker is aligned with respect to the region of interest such that location of the at least one position marker indicates a position of the region of interest. A diagnostic test system includes a reader that obtains light intensity measurement from exposed regions of the test strip, and a data analyzer that performs at least one of (a) identifying ones of the light intensity measurements obtained from the test region based on at least one measurement obtained from the at least one reference feature, and (b) generating a control signal modifying at least one operational parameter of the reader based on at least one measurement obtained from the at least one reference feature.

18 Claims, 9 Drawing Sheets

Related U.S. Application Data

11/280,640, filed on Nov. 16, 2005, now Pat. No. 7,521,260, which is a continuation-in-part of application No. 11/112,807, filed on Apr. 22, 2005, now Pat. No. 8,128,871.

(51) Int. Cl.
  *G01N 33/558* (2006.01)
  *G01N 21/17* (2006.01)
  *G01N 21/64* (2006.01)
  *G01N 21/27* (2006.01)

(52) U.S. Cl.
  CPC ..... *G01N 21/6428* (2013.01); *G01N 21/8483* (2013.01); *G01N 33/558* (2013.01); *G01N 2021/6439* (2013.01); *G01N 2201/062* (2013.01); *G01N 2201/067* (2013.01); *Y10S 435/805* (2013.01); *Y10S 435/823* (2013.01); *Y10S 436/807* (2013.01); *Y10S 436/809* (2013.01); *Y10S 436/81* (2013.01); *Y10S 436/823* (2013.01); *Y10T 436/25125* (2015.01)

(58) Field of Classification Search
  CPC ......... G01N 21/8483; G01N 2201/067; G01N 2201/062; G01N 2021/6439; Y10T 436/25125; Y10S 436/807; Y10S 436/823; Y10S 436/81; Y10S 436/809; Y10S 435/805; Y10S 435/823
  See application file for complete search history.

(56) References Cited

U.S. PATENT DOCUMENTS

| | | |
|---|---|---|
| 4,916,056 A | 4/1990 | Brown et al. |
| 4,960,691 A | 10/1990 | Gordon et al. |
| 5,030,558 A | 7/1991 | Litman et al. |
| 5,132,097 A | 7/1992 | Van Deusen et al. |
| 5,217,832 A | 6/1993 | Joslin et al. |
| 5,281,395 A | 1/1994 | Markart et al. |
| 5,304,813 A | 4/1994 | De Man |
| 5,371,687 A | 12/1994 | Holmes, II et al. |
| 5,424,220 A | 6/1995 | Goerlach-Graw et al. |
| 5,442,169 A | 8/1995 | Kunz |
| 5,514,602 A | 5/1996 | Brooks et al. |
| 5,519,210 A | 5/1996 | Berner et al. |
| 5,550,362 A * | 8/1996 | Sherman ............ G06K 7/10851 235/455 |
| 5,559,041 A | 9/1996 | Kang et al. |
| 5,580,794 A | 12/1996 | Allen |
| 5,602,040 A | 2/1997 | May et al. |
| 5,837,546 A | 11/1998 | Allen et al. |
| 5,856,203 A | 1/1999 | Robinson et al. |
| 5,861,256 A | 1/1999 | Glass et al. |
| 5,961,451 A | 10/1999 | Reber et al. |
| 6,017,767 A | 1/2000 | Chandler |
| 6,136,610 A | 10/2000 | Polito et al. |
| 6,180,409 B1 | 1/2001 | Howard et al. |
| 6,217,744 B1 | 4/2001 | Crosby |
| 6,235,241 B1 | 5/2001 | Catt et al. |
| 6,267,722 B1 | 7/2001 | Anderson et al. |
| 6,268,162 B1 | 7/2001 | Phillips et al. |
| 6,274,323 B1 | 8/2001 | Bruchez et al. |
| 6,281,785 B1 | 8/2001 | Hamaguchi |
| 6,300,141 B1 | 10/2001 | Segal et al. |
| 6,326,144 B1 | 12/2001 | Bawendi et al. |
| 6,377,894 B1 | 4/2002 | Deweese et al. |
| 6,379,622 B1 | 4/2002 | Polak et al. |
| 6,394,952 B1 | 5/2002 | Anderson et al. |
| 6,403,037 B1 | 6/2002 | Chang et al. |
| 6,483,582 B2 | 11/2002 | Modlin et al. |
| 6,561,643 B1 | 5/2003 | Walker et al. |
| 6,585,341 B1 | 7/2003 | Walker et al. |
| 6,607,922 B2 | 8/2003 | LaBorde |
| 6,611,634 B2 | 8/2003 | Herron et al. |
| 6,629,057 B2 | 9/2003 | Zweig et al. |
| 6,630,307 B2 | 10/2003 | Bruchez et al. |
| 6,656,744 B2 | 12/2003 | Pronovost et al. |
| 6,663,833 B1 | 12/2003 | Stave et al. |
| 6,671,428 B1 | 12/2003 | Yang et al. |
| 6,673,622 B1 | 1/2004 | Jina |
| 6,673,630 B2 | 1/2004 | Albarella et al. |
| 6,686,170 B1 | 2/2004 | Flanders et al. |
| 6,713,271 B1 | 3/2004 | Feistel et al. |
| 6,732,917 B1 | 5/2004 | Benz et al. |
| 6,750,963 B2 | 6/2004 | Sampas |
| 6,855,561 B2 | 2/2005 | Jerome et al. |
| 6,875,185 B2 | 4/2005 | Wong et al. |
| 6,966,880 B2 | 11/2005 | Boecker et al. |
| 7,378,285 B2 | 5/2008 | Lambotte et al. |
| 7,521,260 B2 | 4/2009 | Petruno et al. |
| 7,678,566 B2 | 3/2010 | Miyoshi et al. |
| 8,043,867 B2 | 10/2011 | Petruno et al. |
| 8,128,871 B2 | 3/2012 | Petruno et al. |
| 9,243,997 B2 | 1/2016 | Petruno et al. |
| 9,891,217 B2 | 2/2018 | Petruno et al. |
| 9,989,527 B2 | 6/2018 | Petruno et al. |
| 2001/0034068 A1 | 10/2001 | Spivey et al. |
| 2001/0035990 A1 | 11/2001 | Mok et al. |
| 2002/0004246 A1 | 1/2002 | Daniels et al. |
| 2002/0146844 A1 | 10/2002 | Pronovost et al. |
| 2002/0169439 A1 | 11/2002 | Flaherty |
| 2002/0176927 A1 | 11/2002 | Kodas et al. |
| 2003/0003601 A1 | 1/2003 | Some et al. |
| 2003/0082516 A1 | 5/2003 | Straus |
| 2003/0119202 A1 | 6/2003 | Kaylor et al. |
| 2003/0119203 A1 | 6/2003 | Wei et al. |
| 2003/0143580 A1 | 7/2003 | Straus |
| 2003/0171697 A1 | 9/2003 | Smith et al. |
| 2003/0174743 A1 | 9/2003 | Cliché et al. |
| 2003/0175820 A1 | 9/2003 | Smith et al. |
| 2003/0201176 A1 | 10/2003 | Mills et al. |
| 2003/0207454 A1 | 11/2003 | Eyster et al. |
| 2003/0222198 A1 | 12/2003 | Olszak et al. |
| 2004/0012783 A1 | 1/2004 | Morokawa et al. |
| 2004/0014202 A1 | 1/2004 | King et al. |
| 2004/0018637 A1 | 1/2004 | Polito et al. |
| 2004/0043502 A1 | 3/2004 | Song et al. |
| 2004/0063219 A1 | 4/2004 | Bateman et al. |
| 2004/0096169 A1 | 5/2004 | Sone et al. |
| 2004/0151632 A1 | 8/2004 | Badley et al. |
| 2004/0152209 A1 | 8/2004 | Zin et al. |
| 2004/0214347 A1 | 10/2004 | LaBorde et al. |
| 2005/0033196 A1 | 2/2005 | Alroy |
| 2005/0037510 A1 | 2/2005 | Sharrock et al. |
| 2005/0112703 A1 * | 5/2005 | Song ............... G01N 33/54393 435/7.5 |
| 2005/0130164 A1 | 6/2005 | Akimoto et al. |
| 2005/0221504 A1 | 10/2005 | Petruno et al. |
| 2005/0221505 A1 | 10/2005 | Petruno et al. |
| 2006/0014302 A1 | 1/2006 | Martinez et al. |
| 2006/0121625 A1 | 6/2006 | Clemens et al. |
| 2006/0122782 A1 | 6/2006 | Petrilla et al. |
| 2006/0126063 A1 | 6/2006 | Cluzel et al. |
| 2006/0210435 A1 | 9/2006 | Alavie et al. |
| 2006/0216696 A1 | 9/2006 | Goguen |
| 2006/0240541 A1 | 10/2006 | Petruno et al. |
| 2006/0240568 A1 | 10/2006 | Petruno et al. |
| 2007/0081920 A1 | 4/2007 | Murphy et al. |
| 2007/0185679 A1 | 8/2007 | Petruno et al. |
| 2007/0231922 A1 | 10/2007 | Petruno et al. |
| 2009/0180925 A1 | 7/2009 | Petruno et al. |
| 2009/0180926 A1 | 7/2009 | Petruno et al. |
| 2009/0180927 A1 | 7/2009 | Petruno et al. |
| 2009/0180928 A1 | 7/2009 | Petruno et al. |
| 2009/0180929 A1 | 7/2009 | Petruno et al. |
| 2009/0214383 A1 | 8/2009 | Petruno et al. |
| 2012/0129272 A1 | 5/2012 | Petruno et al. |

(56) References Cited

U.S. PATENT DOCUMENTS

2014/0004624 A1    1/2014   Petruno et al.
2016/0313254 A1   10/2016   Petruno et al.

FOREIGN PATENT DOCUMENTS

| JP | H11108927 A | 4/1999 |
|---|---|---|
| JP | 2001033454 A | 2/2001 |
| JP | 2001066277 A | 3/2001 |
| WO | WO 1988/008534 | 11/1988 |
| WO | WO 1995/013531 | 5/1995 |
| WO | WO 1999/041596 | 8/1999 |
| WO | WO 2000/031538 | 6/2000 |
| WO | WO 2001/057502 | 8/2001 |
| WO | WO 2003/065009 | 8/2003 |
| WO | WO 2003/098278 | 11/2003 |
| WO | WO 2004/003527 | 1/2004 |

\* cited by examiner

_US 10,191,043 B2_

METHODS AND SYSTEMS FOR CALIBRATING ILLUMINATION SOURCE OF DIAGNOSTIC TEST SYSTEM

CROSS-REFERENCE TO RELATED APPLICATIONS

This application is a continuation of U.S. application Ser. No. 12/409,877, filed Mar. 24, 2009, which is a divisional of U.S. application Ser. No. 11/280,640, filed Nov. 16, 2005 and issued as U.S. Pat. No. 7,521,260 on Apr. 21, 2009, which is a continuation-in-part of U.S. application Ser. No. 11/112,807, filed Apr. 22, 2005 and issued as U.S. Pat. No. 8,128,871 on Mar. 6, 2012, all of which are incorporated by reference in their entirety.

BACKGROUND

Assay test kits are currently available for testing for a wide variety of medical and environmental conditions or compounds, such as a hormone, a metabolite, a toxin, or a pathogen-derived antigen. FIG. 1 shows a typical lateral flow test strip 10 that includes a sample receiving zone 12, a labeling zone 14, a detection zone 15, and an absorbent zone 20 on a common substrate 22. These zones 12-20 typically are made of a material (e.g., chemically-treated nitrocellulose) that allows fluid to flow from the sample receiving zone 12 to the absorbent zone 22 by capillary action. The detection zone 15 includes a test region 16 for detecting the presence of a target analyte in a fluid sample and a control region 18 for indicating the completion of an assay test.

FIGS. 2A and 2B show an assay performed by an exemplary implementation of the test strip 10. A fluid sample 24 (e.g., blood, urine, or saliva) is applied to the sample receiving zone 12. In the example shown in FIGS. 2A and 2B, the fluid sample 24 includes a target analyte 26 (i.e., a molecule or compound that can be assayed by the test strip 10). Capillary action draws the liquid sample 24 downstream into the labeling zone 14, which contains a substance 28 for indirect labeling of the target analyte 26. In the illustrated example, the labeling substance 28 consists of an immunoglobulin 30 with a detectable particle 32 (e.g., a reflective colloidal gold or silver particle). The immunoglobulin 30 specifically binds the target analyte 26 to form a labeled target analyte complex. In some other implementations, the labeling substance 28 is a non-immunoglobulin labeled compound that specifically binds the target analyte 26 to form a labeled target analyte complex.

The labeled target analyte complexes, along with excess quantities of the labeling substance, are carried along the lateral flow path into the test region 16, which contains immobilized compounds 34 that are capable of specifically binding the target analyte 26. In the illustrated example, the immobilized compounds 34 are immunoglobulins that specifically bind the labeled target analyte complexes and thereby retain the labeled target analyte complexes in the test region 16. The presence of the labeled analyte in the sample typically is evidenced by a visually detectable coloring of the test region 16 that appears as a result of the accumulation of the labeling substance in the test region 16.

The control region 18 typically is designed to indicate that an assay has been performed to completion. Compounds 35 in the control region 18 bind and retain the labeling substance 28. The labeling substance 28 typically becomes visible in the control region 18 after a sufficient quantity of the labeling substance 28 has accumulated. When the target analyte 26 is not present in the sample, the test region 16 will not be colored, whereas the control region 18 will be colored to indicate that assay has been performed. The absorbent zone 20 captures excess quantities of the fluid sample 24.

In the non-competitive-type of lateral flow assay test strip designs shown in FIGS. 2A and 2B, an increase in the concentration of the analyte in the sample results in an increase in the concentration of labels in the test region. Conversely, in competitive-type of lateral flow assay test strip designs, an increase in the concentration of the analyte in the fluid sample results in a decrease in the concentration of labels in the test region.

Although visual inspection of lateral flow assay devices of the type described above are able to provide qualitative assay results, such a method of reading these types of devices is unable to provide quantitative assay measurements and therefore is prone to interpretation errors. Automated and semi-automated lateral flow assay readers have been developed in an effort to overcome this deficiency.

In one approach, a portable lateral flow assay reader performs assays on bodily fluids to detect the presence of certain hormones, glucose, or other bodily fluids of interest. Membrane test strips containing a fluid sample are inserted directly into a receiving port of a reader. The receiving port is shielded to improve sensitivity and reduce the entry of stray or ambient light into the reader. The reader includes a light source and one or more sensors that detect the intensity of light reflected from the detection zones of the test strips that are inserted into the receiving port.

In another approach, a reader detects an intensity of a detection signal arising in one or more measurement zones in a detection zone of a lateral flow assay test strip as a result of the presence of an immobilized labeled target analyte complex. The reader generates a baseline of signal intensity from the measurement zones by interpolating between values of the detection signal outside of the measurement zones and inside of the detection zone. The reader quantifies a value of signal intensity representative of the immobilized labeled target analyte complex with respect to the baseline. In this process, the reader locates a beginning boundary and an ending boundary for the one or more measurement zones on the test strip, allowing an automatic or semi-automatic analytical instrument, or a human reader, to determine certain results of the lateral flow assay. The signals from the measurement zones are quantified or compared with respect to the baseline. Quantified values corresponding to the respective concentration of compounds in different measurement zones may then be compared with one another to detect the presence of antigens in the sample.

The measurements that are made by the above-described lateral flow assay readers are based on signals from regions of the test strips that typically are significantly larger than the regions of interest. As a result, these measurements tend to have high noise levels and, consequently, these measurements may yield inaccurate or incorrect results when low concentrations of analytes are involved.

SUMMARY

In one aspect, the invention features an assay test strip that includes a flow path for a fluid sample, a sample receiving zone, a label, a detection zone, and at least one position marker. The sample receiving zone is coupled to the flow path. The label specifically binds a target analyte. The detection zone is coupled to the flow path and includes a region of interest and an immobilized test reagent that specifically binds the target analyte. The at least one position marker is aligned with respect to the region of interest such that location of the at least one position marker indicates a position of the region of interest.

In one aspect, the invention features an assay test strip that includes a flow path for a fluid sample, a sample receiving zone, a label, a detection zone, and at least one reference feature. The sample receiving zone is coupled to the flow path. The label specifically binds a target analyte. The detection zone is coupled to the flow path and includes an immobilized test reagent that specifically binds the target analyte. The at least one reference feature is exposed for optical inspection and has a calibrated amount of the label.

In another aspect, the invention features a diagnostic test system that includes a housing, a reader, and a data analyzer. The housing includes a port constructed and arranged to receive a test strip. The test strip includes a flow path for a fluid sample, a sample receiving zone coupled to the flow path, a label that specifically binds a target analyte, a detection zone, and at least one reference feature. The detection zone is coupled to the flow path and includes a test region. The test region is exposed for optical inspection and has an immobilized test reagent that specifically binds the target analyte. The reader is operable to obtain light intensity measurements from exposed regions of the test strip when the test strip is loaded in the port. The data analyzer is operable to perform operations including at least one of (a) identifying ones of the light intensity measurements obtained from the test region based on at least one measurement obtained from the at least one reference feature, and (b) generating a control signal modifying at least one operational parameter of the reader based on at least one measurement obtained from the at least one reference feature.

The invention also features a diagnostic test method in accordance with which a test strip is received. The test strip includes a flow path for a fluid sample, a sample receiving zone coupled to the flow path, a label that specifically binds a target analyte, a detection zone, and at least one reference feature. The detection zone is coupled to the flow path and includes a test region. The test region is exposed for optical inspection and has an immobilized test reagent that specifically binds the target analyte. Light intensity measurements are obtained from exposed regions of the test strip. At least one of the following is performed: (a) identifying ones of the light intensity measurements obtained from the test region based on at least one measurement obtained from the at least one reference feature, and (b) generating a control signal modifying the obtaining of light intensity measurements from exposed regions of the test strip based on at least one measurement obtained from the at least one reference feature.

Other features and advantages of the invention will become apparent from the following description, including the drawings and the claims.

DETAILED DESCRIPTION

Figure 1:
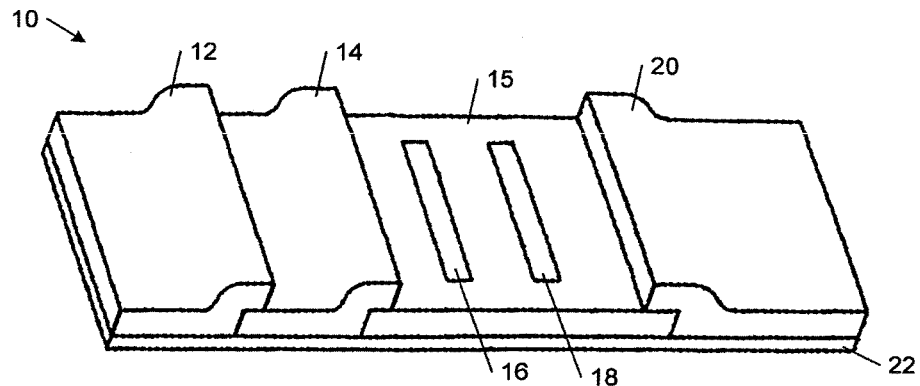
FIG. 1 is a diagrammatic view of a prior art implementation of an assay test strip.
Figure 2A:
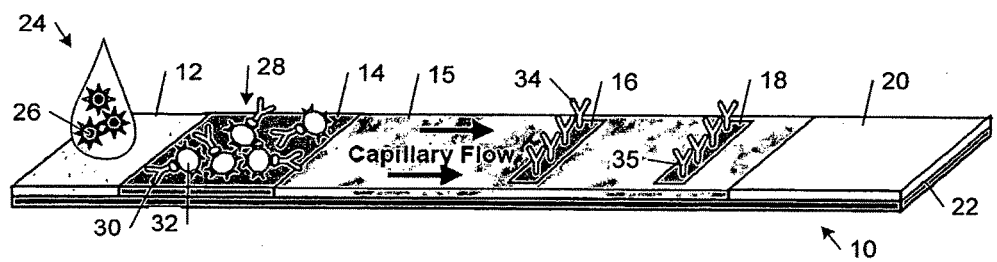
FIG. 2A is a diagrammatic view of a fluid sample being applied to an application zone of the assay test strip shown in FIG. 1.
Figure 2B:
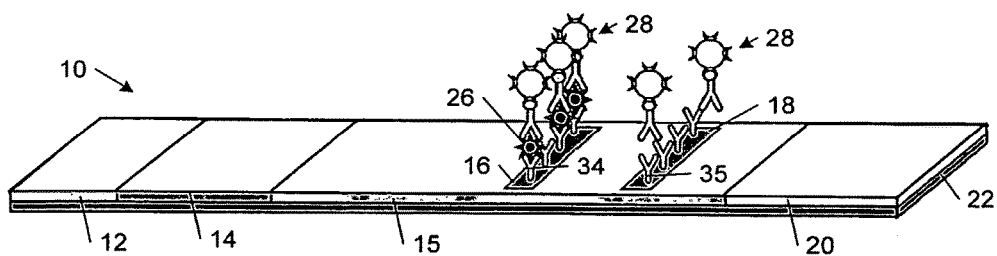
FIG. 2B is a diagrammatic view of the assay test strip shown in FIG. 2A after the fluid sample has flowed across the test strip to an absorption zone.

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

I. Introduction

The embodiments that are described in detail below provide lateral flow assay test strips that have one or more reference features. These embodiments also provide diagnostic test systems that are configured to read such test strips in ways that improve the accuracy and precision with which analytes in a fluid sample may be assayed.

In some embodiments, the reference features are position markers that are aligned with respect to regions of interest in the test strip. These embodiments enable the levels of noise (e.g., noise caused by reflection of light or intrinsic fluorescence from materials in the test strip) in assay measurements to be reduced by restricting the measurements to the regions of interest on the test strip based on measurements obtained from the reference features. In this way, these embodiments increase the signal-to-noise levels of these measurements and, thereby, increase measurement sensitivity and reduce the incidence of erroneous results for low concentrations of analytes.

In some embodiments, the reference features are calibration regions that provide a reference optical response that may be used by embodiments of the diagnostic test system to calibrate one or more components of a diagnostic test system and the assay measurements obtained by such a system and, thereby, increase the accuracy of the lateral flow assay results.

The terms "assay test strip" and "lateral flow assay test strip" encompass both competitive and non-competitive types of lateral flow assay test strips. A lateral flow assay test strip generally includes a sample receiving zone and a detection zone, and may or may not have a labeling zone. In some implementations, a lateral flow assay test strip includes a sample receiving zone that is located vertically above a labeling zone, and additionally includes a detection zone that is located laterally downstream of the labeling zone.

The term "analyte" refers to a substance that can be assayed by the test strip. Examples of different types of analytes include organic compounds (e.g., proteins and amino acids), hormones, metabolites, antibodies, pathogen-derived antigens, drugs, toxins, and microorganisms (e.g., bacteria and viruses).

As used herein the term "label" refers to a substance that has specific binding affinity for an analyte and that has a detectable characteristic feature that can be distinguished from other elements of the test strip. The label may include a combination of a labeling substance (e.g., a fluorescent particle, such as a quantum dot) that provides the detectable characteristic feature and a probe substance (e.g., an immunoglobulin) that provides the specific binding affinity for the analyte. In some implementations, the labels have distinctive optical properties, such as luminescence (e.g., fluorescence) or reflective properties, which allow regions of the test strip containing different labels to be distinguished from one another.

The term "reagent" refers to a substance that reacts chemically or biologically with a target substance, such as a label or an analyte.

The term "capture region" refers to a region on a test strip that includes one or more immobilized reagents.

The term "test region" refers to a capture region containing an immobilized reagent with a specific binding affinity for an analyte.

The term "control region" refers to a capture region containing an immobilized reagent with a specific binding affinity for a label.

II. Diagnostic Test System Architecture

A. Overview

Figure 3:
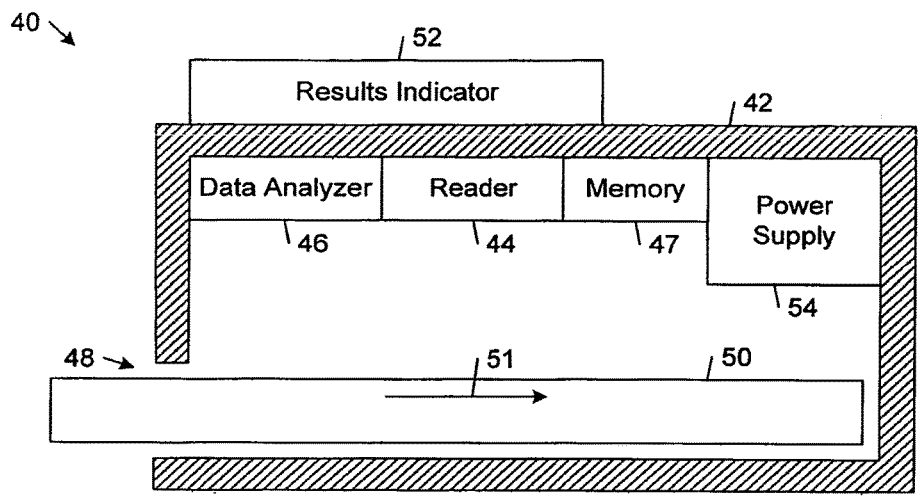
FIG. 3 is a block diagram of an embodiment of a test strip that is loaded into an embodiment of a diagnostic test system.

FIG. 3 shows an embodiment of a diagnostic test system 40 that includes a housing 42, a reader 44, a data analyzer 46, and a memory 47. The housing 42 includes a port 48 for receiving a test strip 50. When the test strip 50 is loaded in the port 48, the reader 44 obtains light intensity measurements from the test strip 50. In general, the light intensity measurements may be unfiltered or they may be filtered in terms of at least one of wavelength and polarization. The data analyzer 46 computes at least one parameter from one or more of the light intensity measurements. A results indicator 52 provides an indication of one or more of the results of an assay of the test strip 50. In some implementations, the diagnostic test system 40 is fabricated from relatively inexpensive components enabling it to be used for disposable or single-use applications.

The housing 42 may be made of any one of a wide variety of materials, including plastic and metal. The housing 42 forms a protective enclosure for the reader 44, the data analyzer 46, the power supply 54, and other components of the diagnostic test system 40. The housing 42 also defines a receptacle that mechanically registers the test strip 50 with respect to the reader 44. The receptacle may be designed to receive any one of a wide variety of different types of test strips 50, including test strips of the type shown in FIG. 1.

In the illustrated embodiments, each of the test strips 50 is a non-competitive type of assay test strip that supports lateral flow of a fluid sample along a lateral flow direction 51 and includes a labeling zone containing a labeling substance that binds a label to a target analyte and a detection zone that includes at least one test region containing an immobilized substance that binds the target analyte. One or more areas of the detection zone, including at least a portion of the test region, are exposed for optical inspection by the reader 44. The exposed areas of the detection zone may or may not be covered by an optically transparent window.

In other embodiments, the test strips are competitive type of lateral flow assay test strips in which the concentrations of the label in the test region decreases with increasing concentration of the target analyte in the fluid sample. Some of these embodiments include a labeling zone, whereas others of these implementations do not include a labeling zone.

Some of these competitive lateral flow assay test strip embodiments include a labeling zone that contains a label that specifically binds target analytes in the fluid sample, and a test region that contains immobilized target analytes as opposed to immobilized test reagents (e.g., antibodies) that specifically bind any non-bound labels in the fluid sample. In operation, the test region will be labeled when there is no analyte present in the fluid sample. However, if target analytes are present in the fluid sample, the fluid sample analytes saturate the label's binding sites in the labeling zone, well before the label flows to the test region. Consequently, when the label flows through the test region, there are no binding sites remaining on the label, so the label passes by and the test region remains unlabeled.

In other competitive lateral flow assay test strip embodiments, the labeling zone contains only pre-labeled analytes (e.g., gold adhered to analyte) and the test region contains immobilized test reagents with an affinity for the analyte. In these embodiments, if the fluid sample contains unlabeled analyte in a concentration that is large compared to the concentration of the pre-labeled analyte in the labeling zone, then label concentration in the test region will appear proportionately reduced.

The reader 44 includes one or more optoelectronic components for optically inspecting the exposed areas of the detection zone of the test strip 50. In some implementations, the reader 44 includes at least one light source and at least one light detector. In some implementations, the light source may include a semiconductor light-emitting diode and the light detector may include a semiconductor photodiode. Depending on the nature of the label that is used by the test strip 50, the light source may be designed to emit light within a particular wavelength range or light with a particular polarization. For example, if the label is a fluorescent label, such as a quantum dot, the light source may be designed to illuminate the exposed areas of the detection zone of the test strip 50 with light in a wavelength range that induces fluorescent emission from the label. Similarly, the light detector may be designed to selectively capture light from the exposed areas of the detection zone. For example, if the label is a fluorescent label, the light detector may be designed to selectively capture light within the wavelength range of the fluorescent light emitted by the label or with light of a particular polarization. On the other hand, if the label is a reflective-type label, the light detector may be designed to selectively capture light within the wavelength range of the light emitted by the light source. To these ends, the light detector may include one or more optical filters that define the wavelength ranges or polarizations axes of the captured light.

The data analyzer 46 processes the light intensity measurements that are obtained by the reader 44. In general, the data analyzer 46 may be implemented in any computing or processing environment, including in digital electronic circuitry or in computer hardware, firmware, or software. In some embodiments, the data analyzer 46 includes a processor (e.g., a microcontroller, a microprocessor, or ASIC) and an analog-to-digital converter. In the illustrated embodiment, the data analyzer 46 is incorporated within the housing 42 of the diagnostic test system 40. In other embodiments, the data analyzer 46 is located in a separate device, such as a computer, that may communicate with the diagnostic test system 40 over a wired or wireless connection.

In general, the results indicator 52 may include any one of a wide variety of different mechanisms for indicating one or more results of an assay test. In some implementations, the results indicator 52 includes one or more lights (e.g., light-emitting diodes) that are activated to indicate, for example, a positive test result and the completion of the assay test (i.e., when sufficient quantity of labeling substance 28 has accumulated in the control region). In other implementations, the results indicator 52 includes an alphanumeric display (e.g., a two or three character light-emitting diode array) for presenting assay test results.

A power supply 54 supplies power to the active components of the diagnostic test system 40, including the reader 44, the data analyzer 46, and the results indicator 52. The power supply 54 may be implemented by, for example, a replaceable battery or a rechargeable battery. In other embodiments, the diagnostic test system may be powered by an external host device (e.g., a computer connected by a USB cable).

Figure 4:
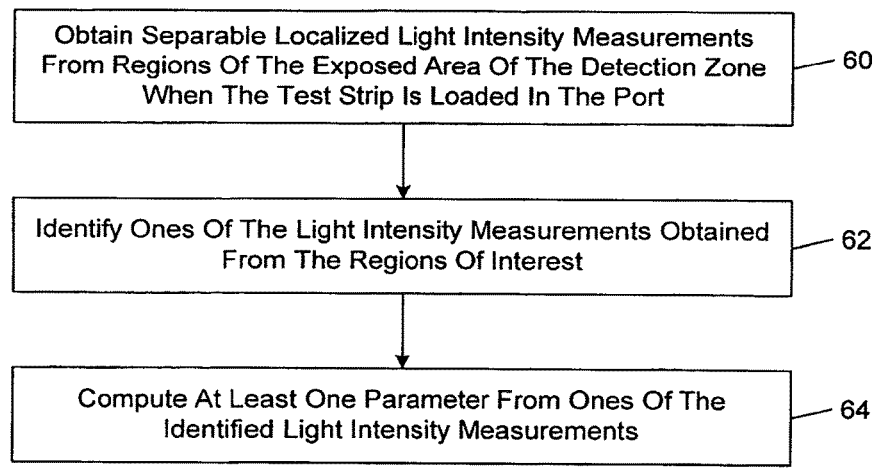
FIG. 4 is a flow diagram of an embodiment of a diagnostic test method.

FIG. 4 shows an embodiment of a diagnostic test method that is executable by the implementations of the diagnostic test system 40 described below. In accordance with this method, the reader 44 obtains separable localized light intensity measurements from regions of the exposed area of the detection zone of the test strip 50 when the test strip 50 is loaded in the port 48 of the diagnostic test system 40 (FIG. 4, block 60). As used herein, the term "separable localized light intensity measurements" refers to the ability of the reader 44 to transmit or record the light intensity measurements from respective localized regions of the test strip in a way that allows the data analyzer 46 to individually analyze each of the light intensity measurements.

In some embodiments in accordance with the invention, each of the separable localized regions from which the light intensity measurements are obtained by the reader 44 is characterized by at least one surface dimension that is smaller than the dimension of the exposed area of the detection zone that is transverse to the lateral flow direction 51. In some implementations, each of these localized regions has a surface dimension that is approximately the same size or smaller than the narrowest dimension of a region of interest in the detection zone 15 (e.g., the test region, the control region, or a region of an immobilized labeled or unlabeled complex).

After the reader 44 has obtained light intensity measurements from such localized regions of interest in the detection zone 15 (FIG. 4, block 60), the data analyzer 46 identifies ones of the light intensity measurements obtained from the regions of interest (FIG. 4, block 62). In this process, the data analyzer 46 isolates the measurements corresponding to regions of interest from the measurements corresponding to other regions of the test strip 50. The isolated measurements have higher signal-to-noise ratios than aggregated measurements that include measurements from regions outside of the regions of interest.

The data analyzer 46 then computes at least one parameter from ones of the identified light intensity measurements (FIG. 4, block 64). Exemplary parameters include peak intensity and aggregate intensity values. Since the measurements that are used to compute these parameters have higher signal-to-noise ratios, they characterize the region of interest with greater accuracy and, thereby, improve the results of the lateral flow assay.

B. An Exemplary Implementation of the Diagnostic Test System

Figure 5A:
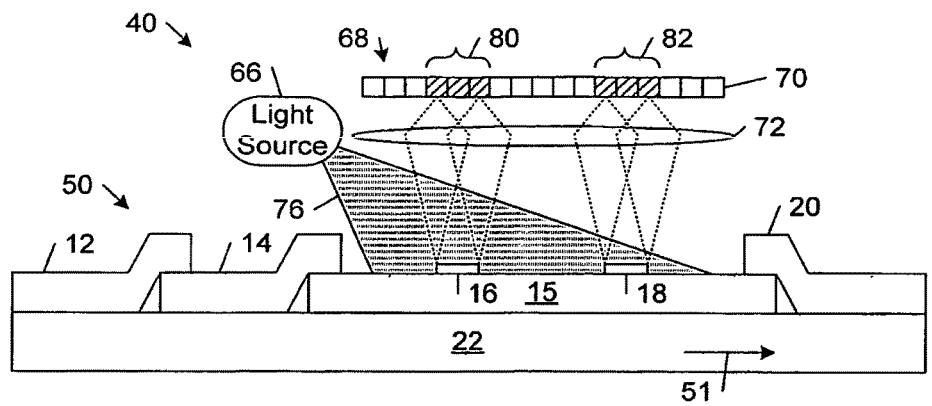
FIG. 5A is a diagrammatic side view of an implementation of the diagnostic test system shown in FIG. 3 that includes a two-dimensional light detector array obtaining light intensity measurements from regions of a test strip.

FIG. 5A shows an exemplary implementation of the diagnostic test system 40 that includes a light source 66, a two-dimensional array 68 of light detectors 70, and a lens 72. In FIG. 5A, the gross structural features of the test strip 50 are substantially the same as the corresponding features the test strip 10, which is shown in FIG. 1. In particular, the test strip 50 includes the sample receiving zone 12, the labeling zone 14, the detection zone 15, and the absorbent zone 20 on the common substrate 22. In the illustrated implementation, a substantial portion of the detection zone 15 is exposed for optical inspection.

In operation, the light source 66 illuminates with light 76 the exposed portion of the detection zone 15, including the test region 16 and the control region 18 of the test strip 50. The illuminating light 76 may be broadband or narrowband and may be polarized or non-polarized. The light detector array 68 obtains separable localized light intensity measurements from the illuminated regions of the detection zone 15. In general, the light intensity measurements may be unfiltered or they may be filtered in terms of at least one of wavelength and polarization. The light detector array 68 may be synchronized with the light source 66. In general, the light detector array 68 may measure light intensity while the detection zone 15 is being illuminated or after the light source 66 has illuminated the detection zone 15. Light reflected or fluorescing from the detection zone 15 is focused by the lens 72 onto the individual light detectors 70 of the light detector array 68. Each of the light detectors 70 receives light from a respective localized region of the detection zone 15. That is, each light detector 70 is able to resolve or separably image a respective localized region of the detection zone 15. In this implementation, the localized regions are characterized by a surface dimension that is at most as large as the narrowest dimension of the test and control regions 16, 18 (i.e., the dimensions of regions 16, 18 that are along the lateral flow direction). In the illustrated implementations, the localized regions are characterized by square dimensions that are approximately equal to one-third of the size of the test and control regions 16, 18 along the lateral flow direction. The light detectors 70 produce signals representative of the amount of light received from the respective localized regions. These signals may be stored in a memory or they may be transmitted to the data analyzer 46 for processing.

Figure 5B:
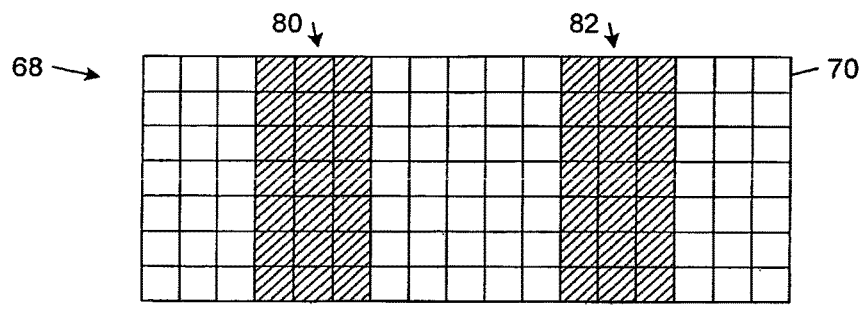
FIG. 5B is a diagrammatic view of the two-dimensional light detector array shown in FIG. 5A in which ones of the light detectors that are positioned to obtain light intensity measurements from the test region and the control region are highlighted.

As shown in FIGS. 5A and 5B, the reflected or fluorescing light from the test region 16 is received by only a subset 80 of the light detectors 70 in the array 68. Similarly, the reflected or fluorescing light from the control region 18 is received by only a subset 82 of the light detectors 70 in the array 68. Thus, the signals from the light detectors in the subsets 80, 82 provide relatively low noise light intensity measurements of the light reflected or fluorescing from the test region 16 and the control region 18, respectively.

Figure 6:
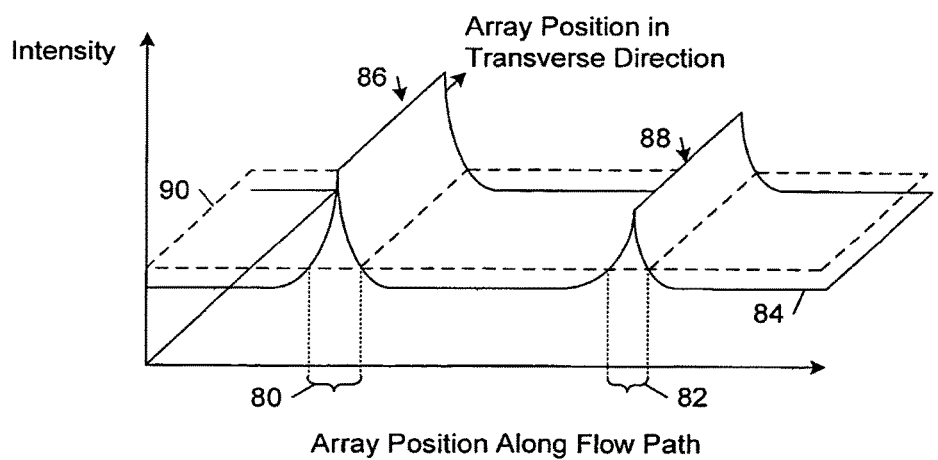
FIG. 6 is an exemplary graph of light intensity plotted as a function of position in the two-dimensional light detector array shown in FIGS. 5A and 5B.

The data analyzer 46 is operable to process the signals that are generated by the individual light detectors 70 to identify the ones of the light intensity measurements that are obtained from the regions of interest (e.g., the test region 16 and the control region 18). Referring to FIG. 6, in one illustrative example, the light detector, array 68 produces a set of light intensity signals that are represented by a three-dimensional surface 84. In this example, the surface 84 includes higher intensity measurements 86, 88 from locations of the detection zone 15 corresponding to the subsets 80, 82 of the light detectors 70 in the light detector array 68. With respect to this example, the data analyzer 46 may identify the light intensity measurements that are obtained from the test region 16 and the control region 18 by thresholding the surface 84 at an intensity threshold level 90. In some implementations, the threshold that is used in the thresholding process is constant across the strip or region of interest. For example, in some implementations, the threshold may be slanted or have local variations to account for variations in illumination or diffusion of the analytes. The ones of the light intensity measurements that are above the threshold level 90 are identified as having come from the test region 16 and the control region 18. Additional information, such as the relative positions of the light detector array 68 from which the identified ones of the light intensity measurements were obtained, may be used by the data analyzer 46 to correlate the identified light intensity measurements with the test region 16 and the control region 18.

III. Position Markers on a Test Strip and Reading Same

A. Overview

In some embodiments, the test strip 50 includes one or more reference features that serve as position markers, which are aligned with respect to regions of interest in the test strip. These embodiments enable the levels of noise (e.g., noise caused by reflection of light or intrinsic fluorescence from materials in the test strip) in lateral flow assay measurements to be reduced by restricting the measurements to the regions of interest on the test strip based on measurements obtained from the reference features. In this way, these embodiments increase the signal-to-noise levels of these measurements and, thereby, increase measurement sensitivity and reduce the incidence of erroneous results for low concentrations of analytes.

Figure 7:
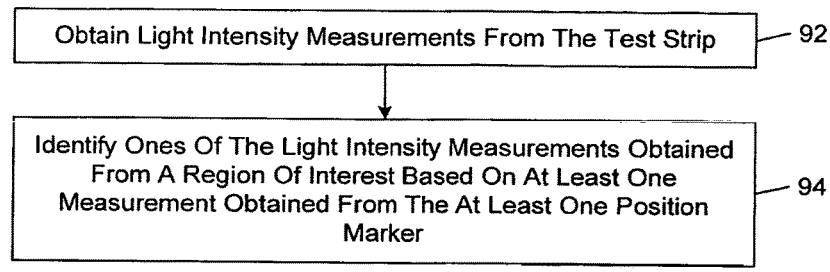
FIG. 7 is a flow diagram of an embodiment of a method of reading a test strip having at least one position marker.

FIG. 7 shows an embodiment of a method by which the diagnostic test system 40 (FIG. 3) reads a test strip having at least one position marker.

In accordance with this method, the reader 44 obtains light intensity measurements from the test strip (FIG. 7, block 92). In the implementation shown in FIG. 5A, the light source 66 illuminates the exposed portion of the detection zone 15, including the test region 16 and the control region 18 of the test strip 50, with light 76. The illuminating light 76 may be broadband or narrowband and may be polarized or non-polarized. The light detector array 68 then obtains separable localized light intensity measurements from the illuminated regions of the detection zone 15.

The data analyzer 46 identifies ones of the light intensity measurements that are obtained from a region of interest (e.g., the test region 16 or the control region 18) based on at least one measurement that is obtained from the at least one position marker (FIG. 7, block 94). In this process, the data analyzer 46 may identify the ones of the light intensity measurements that are obtained from a region of interest based on predetermined information about the spatial relationship between the region of interest and the at least one position marker.

In general, each of the position markers may be implemented by any type of feature that has a different optical, electrical, or mechanical characteristic than the adjacent regions of the test strip surface.

B. Optical Position Markers

In some implementations, an optical position marker may have a detectable optical response that is different from the optical response of adjacent surface regions. For example, an optical position marker may have a greater reflection or emission than adjacent surface regions with respect to light within a specified wavelength range (e.g., the visible wavelength range: 390 nm to 770 nm). In other implementations, an optical position marker may have a lower reflection or emission than adjacent surface regions with respect to light within the specified wavelength range. In some implementations, the optical position marker is capable of fluorescent emission within a first wavelength range, whereas the adjacent surface regions are capable of fluorescent emission within a second wavelength range different from the first wavelength range or with an intensity that is significantly lower than the intensity of fluorescent emission by the optical position marker within the first wavelength range.

Figure 8:
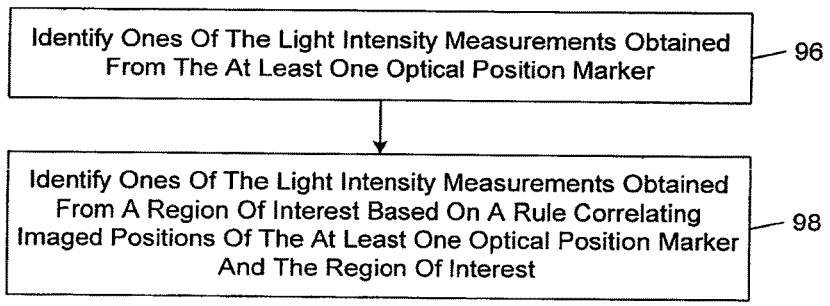
FIG. 8 is a flow diagram of an embodiment of a method of identifying light intensity measurements that are obtained from a region of interest based on light intensity measurements that are obtained from at least one optical position marker.

FIG. 8 shows an embodiment of a method by which the data analyzer 46 identifies ones of the light intensity measurements that are obtained from a region of interest in the detection zone 15 based on intensity measurements that are obtained from at least one optical position marker that is aligned with respect to the region of interest along the lateral flow direction 51.

In accordance with this embodiment, the data analyzer 46 identifies ones of the light intensity measurements that are obtained from the at least one optical position marker (FIG. 8, block 96).

The data analyzer 46 may identify the light intensity measurements that are obtained from the at least one optical position marker in any of a wide variety of different ways that depend on the implementation of the optical position marker and the other regions in the detection zone. As explained above, each of the optical position markers may be implemented by any type of feature on a surface of the test strip 50 that has a different optical characteristic than the adjacent regions of the test strip surface. In some implementations, the optical position markers are composed of quantum dots that exhibit fluorescent emission with narrow wavelength ranges or other optically recognizable media. The optical position markers may be formed on the exposed surface of the test strip 50 in any of a wide variety of different ways, including silk screening and other printing or deposition methods. The data analyzer 46 may identify the ones of the light intensity measurements that correspond to the optical position marker by identifying the light intensity measurements that have one or more predetermined attributes, such as exhibiting a characteristic pattern of light intensity variations across the test strip along the lateral flow direction or having the highest relative intensities within a specified wavelength range.

After identifying the light intensity measurements that are obtained from the at least one optical position marker (FIG. 8, block 96), the data analyzer 46 identifies ones of the light intensity measurements that are obtained from the region of interest based on a rule correlating imaged positions of the at least one optical position marker and the region of interest (FIG. 8, block 98). In some implementations, the at least one optical position marker encodes at least one position along the lateral flow direction. In these implementations, the data analyzer 46 infers the imaged position of the region of interest based on the positions that are encoded by the optical position markers. For example, the encoded position may correspond to one or both of the beginning and ending locations of the region of interest along the lateral flow direction. In these implementations, the data analyzer 46 may infer that the region of interest is located after, before or between the locations demarcated by the at least one optical position marker.

Figure 9:
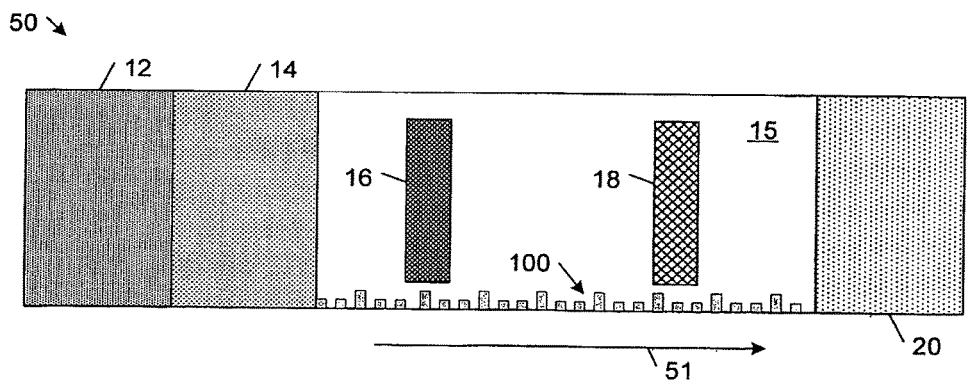
FIG. 9 is a diagrammatic view of an implementation of the test strip shown in FIG. 3.

FIG. 9 shows an implementation of the test strip 50 that includes an exemplary set of optical position markers 100 that are spaced regularly along the edge of the test strip 50. The optical position markers 100 include features that have a different reflection or emission characteristic than the surface of the test strip 50. As a result, the measurements that are obtained near the edge of the test strip 50 vary in intensity in accordance with the pattern of the optical position markers 100. In this way, the optical position markers 100 encode positions along the test strip 50 in the lateral flow direction 51. With respect to the implementation shown in FIG. 9, the data analyzer 46 may determine the encoded positions along the lateral flow direction by incrementing a position counter with each intensity variation cycle (e.g., peak-to-valley) in the light intensity measurements obtained from the edge of the detection zone 15.

In these implementations, the data analyzer 46 correlates the light intensity measurements with the positions along the test strip 50 in the lateral flow direction 51. The location correlation information may be stored in a lookup table that is indexed by the position counter value. Based on this information and on the predetermined information correlating the locations of the regions of interest with the light intensity contrast pattern produced by the optical position markers 100, the data analyzer 46 can identify the ones of the light intensity measurements corresponding to the regions of interest.

In other implementations, the optical position markers 100 may encode position information in variations in the lengths of the optical position markers along the lateral flow direction 51. Alternatively, the optical position markers 100 may encode position information in variations in the spacing between adjacent ones of the optical position markers 100 along the lateral flow direction 51.

Figure 10:
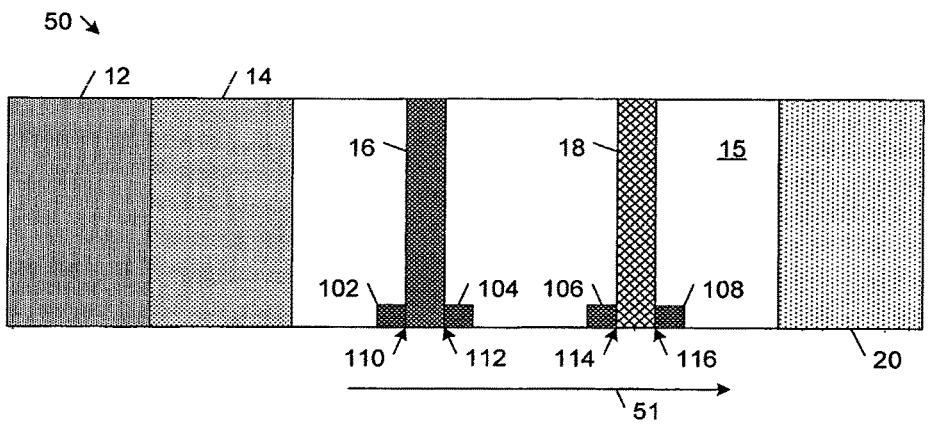
FIG. 10 is a diagrammatic view of an implementation of the test strip shown in FIG. 3.

FIG. 10 shows an implementation of the test strip 50 that includes an exemplary set of optical position markers 102, 104, 106, 108 that are positioned adjacent to the test region 16 and the control region 18. In particular, the optical position marker 102 is positioned adjacent to an upstream edge 110 of the test region 16 and the optical position marker 104 is positioned adjacent to a downstream edge 112 of the test region 16. Similarly, the optical position marker 106 is positioned adjacent to an upstream edge 114 of the control region 18 and the optical position marker 108 is positioned adjacent to a downstream edge 116 of the control region 18. In the illustrated embodiment, the optical position markers 102-108 are beside one edge of the detection zone 15.

In the illustrated embodiment, the optical position markers 102-108 have square shapes. In general, however, the optical position markers 102-108 may have any type of shape, including a polygonal (e.g., rectangular) shape and a curved (e.g., elliptical or circular) shape.

In some implementations, the data analyzer 46 is operable to identify the light intensity measurements that are obtained from the optical position markers 102-108 based on the sizes, shapes, and/or locations of the optical position markers 102-108. For example, the data analyzer 46 may identify the light intensity measurements by locating square regions in an image of the detection zone 15 that is captured by the light detector array 68. In other implementations, the data analyzer 46 may identify the light intensity measurements that are obtained from the optical position markers 102-108 based on one or more attributes (e.g., relative intensity, wavelength, or decay profile) of the light reflected or fluorescing from the optical position markers 102-108.

The data analyzer 46 readily may determine the bounds of the regions of interest 16, 18 based on the edges of the optical position markers 102-108 in an image that is captured by the light detector array 68. For example, with respect to the implementation illustrated in FIG. 10, the data analyzer 46 identifies the test region 16 as the transverse region between the optical position markers 102, 104 and identifies the control region 18 as the transverse region between the optical position markers 106, 108. If only the upstream optical position markers 102, 106 were present, the data analyzer 46 would be configured to identify the regions of interest 16, 18 as corresponding to the transverse regions immediately following the optical position markers 102, 106 with respect to the lateral flow direction. Similarly, if only the downstream optical position markers 104, 108 were present, the data analyzer 46 would be configured to identify the regions of interest 16, 18 as corresponding to the transverse regions immediately preceding the optical position markers 104, 108 with respect to the lateral flow direction 51.

Figure 11:
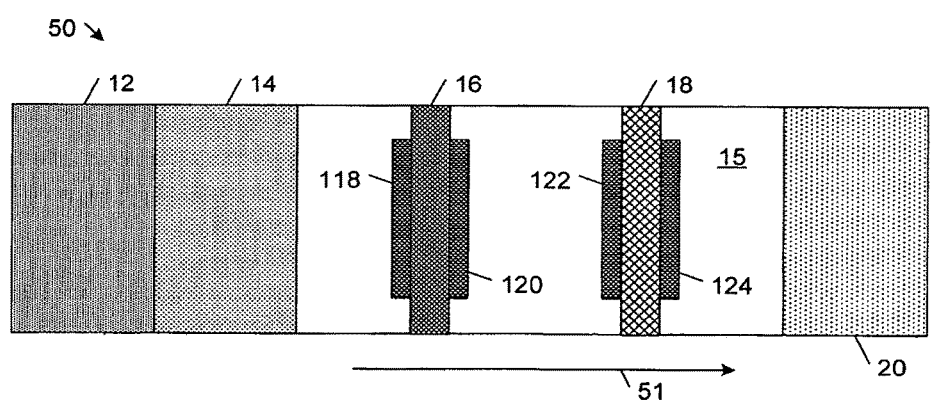
FIG. 11 is a diagrammatic view of an implementation of the test strip shown in FIG. 3.

In the implementation of the test strip 50 that is illustrated in FIG. 10, the optical position markers 102-108 are located beside an edge of the detection zone 15. FIG. 11 shows another implementation of the test strip 50 in which the optical position markers 118, 120, 122, 124 are located centrally over the flow path in the detection zone 15. The optical position markers 118-124 are elongate in the transverse direction perpendicular to the lateral flow direction 51. In other respects, the optical position markers 118-124 may be implemented in the same way as the optical position markers 102-108.

Figure 12A:
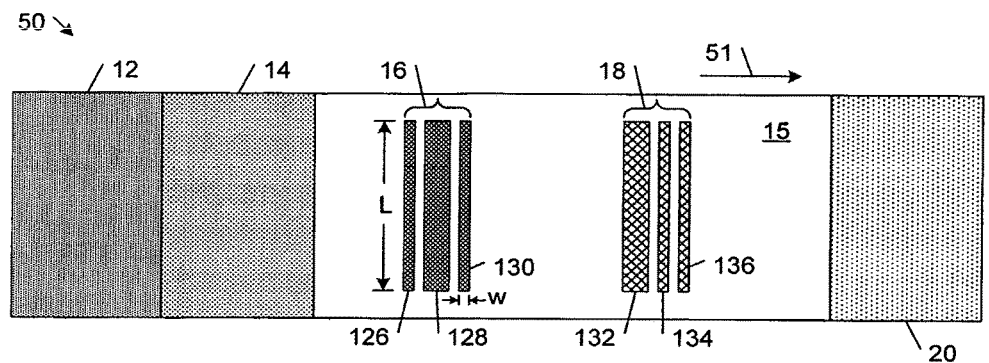
FIG. 12A is a diagrammatic view of an implementation of the test strip shown in FIG. 3.

FIG. 12A shows an embodiment of the test strip 50 in which respective optical position markers are formed by the spatial arrangement of the immobilized test reagent in the test region 16 and the spatial arrangement of the immobilized test reagent in the control region 18. In particular, the test region 16 includes three discrete, spaced-apart code areas 126, 128, 130 in which the test reagent is immobilized. Similarly, the control region 18 includes three discrete, spaced-apart code areas 132, 134, 136 in which the control reagent is immobilized. Each of the code areas 126-136 has a rectangular shape with the same length (L) but varying width. In this exemplary embodiment, each of the code areas has a width that is an integer multiple of a unit width (w). For example, the widths of the code areas 126, 130, 134, and 136 are equal to the unit width w, whereas the widths of the code areas 128, 132 are equal to 3w. The position information is encoded in the varying widths of the code areas of the test region 16 and the control region 18.

Figure 12B:
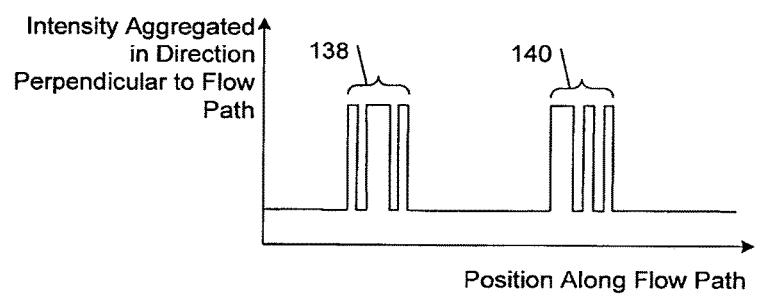
FIG. 12B is a graph of light intensity plotted as a function of position along the test strip shown in FIG. 12A.

FIG. 12B shows a graph of aggregate light intensity plotted as a function of position along the lateral flow direction 51 of test strip shown in FIG. 12A. With respect to this example, the light detector array 68 of the diagnostic test system 20 shown in FIG. 5A captures a first signature light code pattern 138 from the code areas 126-130 of the test region 16 and a second signature light pattern 140 from the code areas 132-136 of the control region 18. The data analyzer 46 determines the widths of the code areas 126-136 from the signature light patterns 138, 140 and translates the widths into code values that uniquely identify the test region 16 and the control region 18. For example, from the signature light pattern 138, the data analyzer 46 determines that the widths of the code areas 126-130 are w, 3w, and w and translates these widths into the code value 131. From the signature light pattern 140, the data analyzer 46 determines that the widths of the code areas 132-136 are 3w, w, and w and translates these widths into the code value 311. In some embodiments, the code values identifying the test region 16 and the control region 18 are stored in a lookup table, which the data analyzer 46 may query to determine the locations of the test region 16 and the control region 18.

In general, the immobilized test reagent and the immobilized control reagent may be arranged in any one-dimensional or two-dimensional pattern that uniquely identifies the test region 16 and the control region 18, respectively. In some implementations, the immobilized reagents of the test and control regions 16, 18 are spatially arranged to form one- or two-dimensional bar code symbols. In some embodiments, the bar codes symbols are patterns of parallel bars and spaces of various widths that represent data elements or characters. Typically, the bars represent strings of binary ones and the spaces represent strings of binary zeros. A one-dimensional bar code symbol (e.g., a UPC bar code symbol) typically contains a series of bars and spaces that vary only in a single dimension. In two-dimensional bar codes (e.g., a PDF417 bar code symbol, a Code 1 bar code symbol, and a Maxicode bar code symbol), the bar code patterns vary in two dimensions. With respect these embodiments, the diagnostic test system 40 implements the bar code decoding process corresponding to the bar coding method that is used to create the code areas of the test and control regions 16, 18.

In addition to identifying the locations of the test and control regions 16, 18 in the detection zone 15, the code areas may encode additional information relating to the test strip in general (e.g., date and place of manufacture), the test and control regions in particular (e.g., the type of target analyte that may be assayed), or to methods of reading the test strip (e.g., predetermined calibration values or scaling values for adjusting the measurement results or interpreting the measurement results).

C. Electrical Position Markers

In some embodiments, the test strip 50 includes electrical position markers that are aligned with respective regions of interest on the test strip. With respect to these embodiments, the data analyzer 46 identifies the ones of the light intensity measurements that are obtained from the respective regions of interest based on predetermined information about the spatial relationship between the regions of interest and the corresponding electrical position markers.

Figure 13A:
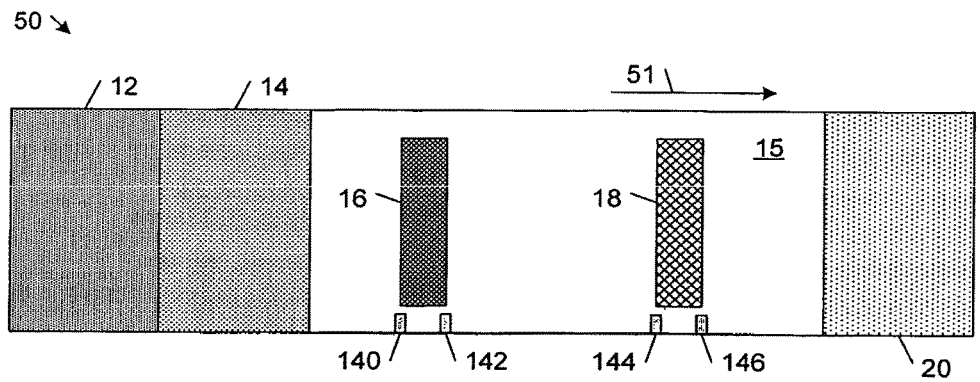
FIG. 13A is a diagrammatic view of an implementation of the test strip shown in FIG. 3.

FIG. 13A shows an implementation of the test strip 50 that includes an exemplary set of electrical position markers 140, 142, 144, 146 that are spaced along the edge of the test strip 50. The electrical position markers 140-146 include features that have a different electrical characteristic than the adjacent areas on the surface of the test strip 50. As a result, the measurements that are obtained near the edge of the test strip 50 vary in electrical response in accordance with the pattern of the electrical position markers 140-146. With respect to these embodiments, the diagnostic test system 40 (FIG. 3) includes a detection system that is capable of detecting the electrical position markers. In general, any type of electrical conductor detection method may be used to detect the electrical position markers, including current, voltage, resistance, and capacitance based measurement methods.

Figure 13B:
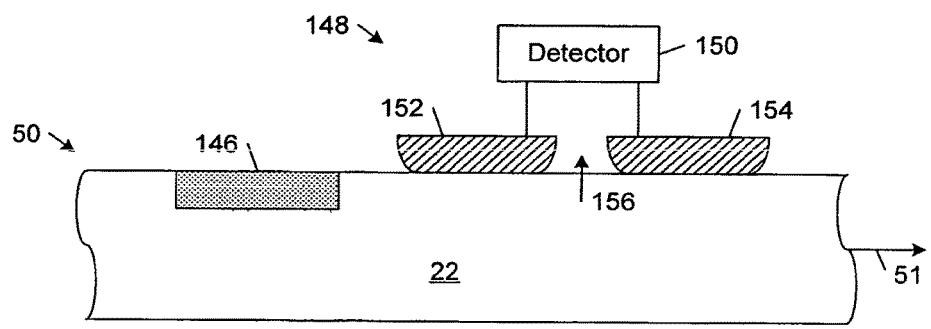
FIG. 13B is a diagrammatic view of a detection system on a portion of the test strip shown in FIG. 13A.

FIG. 13B shows an embodiment of a detection system 148 on a portion of an embodiment of the test strip shown in FIG. 13A. The detection system 148 includes a detector 150, a first electrical contact 152, and a second electrical contact 154. The first and second electrical contacts 152, 154 are electrically connected to the detector 150 and are separated from one another by an air gap 156, which forms an open circuit. The detector 150 may include any type of circuit (e.g., an ohmmeter, a voltmeter, and an ammeter) that is capable of detecting when an electrical connection is formed across the air gap 156. In these embodiments, the top surface of the test strip is formed of a material with a high electrical resistance except at the locations of the electrical position markers 140-146.

Figure 13C:
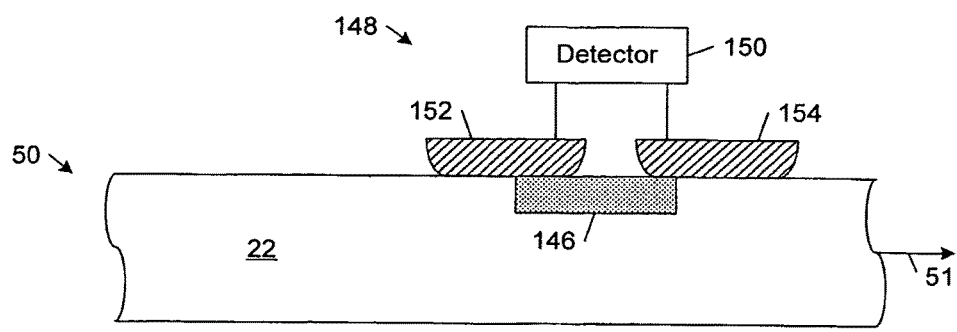
FIG. 13C is a diagrammatic view of the detection system on a different portion of the test strip shown in FIG. 13B.

In operation, at least one of the detection system 148 and the test strip 50 is moved relative to the other in a direction parallel to the lateral flow direction 51. The first and second electrical contacts 152, 154 slide over the top surface of the test strip. In some implementations, the first and second electrical contacts 152, 154 are urged (e.g., by springs) against the top surface of the test strip. In the position shown in FIG. 13B, the first and second electrical contacts 152, 154 are connected only by the material of the top surface of the test strip. In this position, the detector 150 is configured to determine that there is an open circuit between the first and second electrical contacts 152, 154. In the position shown in FIG. 13C, on the other hand, the first and second electrical contacts 152, 154 are connected by the electrical position marker 146. In this position, the detector 150 is configured to determine that there is a closed circuit between the first and second electrical contacts 152, 154.

The detector 150 may determine whether there is an open circuit or a closed circuit between the first and second electrical contacts 152, 154 by comparing an electrical measurement (e.g., current, voltage, or resistance) between the first and second electrical contacts 152, 164 to a threshold value. For example, the detector may determine that there is an open circuit between the first and second electrical contacts 152, 154 when the measured electrical resistance value is greater than or equal to a threshold resistance value and that there is a closed circuit between the first and second electrical contacts 152, 154 when the measured electrical resistance value is below the threshold value.

In the embodiment shown in FIG. 13A, the electrical position markers 140-146 are aligned with the upstream and downstream edges of the test region 16 and the control region 18 along the lateral flow direction 51. In this way, the data analyzer 46 readily may determine that the test and control regions 16, 18 are located between the detected positions of the electrical position markers 140, 142 and 144, 146, respectively.

In other embodiments, the electrical position markers may encode position information in different ways. For example, in some embodiments, the electrical position markers may be positioned at regularly spaced locations along the edge of the test strip 50. As a result, the electrical measurements that are obtained near the edge of the test strip 50 vary in value in accordance with the pattern of the electrical position markers. In this way, the electrical position markers encode positions along the test strip 50 in the lateral flow direction 51. With respect to these embodiments, the data analyzer 46 may determine the encoded positions along the lateral flow direction 51 by incrementing a position counter with each measurement variation cycle (e.g., peak-to-valley) in the electrical measurements obtained from the edge of the detection zone 15.

D. Mechanical Position Markers

In some embodiments, the test strip 50 includes mechanical position markers that are aligned with respective regions of interest on the test strip. With respect to these embodiments, the data analyzer 46 identifies the ones of the light intensity measurements that are obtained from the respective regions of interest based on predetermined information about the spatial relationship between the regions of interest and the corresponding mechanical position markers.

Figure 14A:
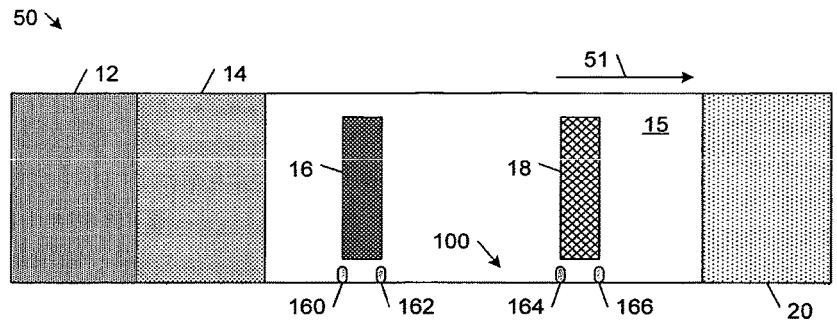
FIG. 14A is a diagrammatic view of an implementation of the test strip shown in FIG. 3.

FIG. 14A shows an implementation of the test strip 50 that includes an exemplary set of mechanical position markers 160, 162, 164, 166 that are spaced along the edge of the test strip 50. The mechanical position markers 160-166 include features that have a different surface profile than the adjacent areas on the surface of the test strip 50. As a result, the measurements that are obtained near the edge of the test strip 50 vary in mechanical response in accordance with the pattern of the mechanical position markers 160-166. With respect to these embodiments, the diagnostic test system 40 (FIG. 3) includes a detection system that is capable of detecting the mechanical position markers. In general, any type of detection method that is responsive to variations in surface profile may be used to detect the mechanical position markers, including spring contact based methods and mechanical transducer based methods.

Figure 14B:
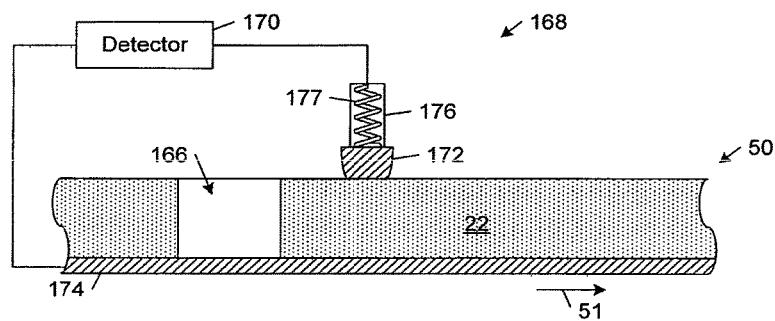
FIG. 14B is a diagrammatic view of a detection system on a portion of the test strip shown in FIG. 14A.

FIG. 14B shows an embodiment of a detection system 168 on a portion of an embodiment of the test strip shown in FIG. 14A. The detection system 168 includes a detector 170, a first electrical conductor 172, and a second electrical conductor 174. The first and second electrical conductors 172, 174 are electrically connected to the detector 170 and are separated from one another by the substrate of the test strip 50. The first electrical conductor 172 is attached to a spring-loaded piston 176 and the second electrical conductor 174 is an electrically conducting support member for the test strip 50. In other embodiments, the first electrical conductor 172 may be implemented by an electrically conducting brush electrode. The detector 170 may include any type of circuit (e.g., an ohmmeter, a voltmeter, and an ammeter) that is capable of detecting when the first and second electrical conductors are electrically connected together. In these embodiments, the test strip is formed of a material with a high electrical resistance and the mechanical position markers 160-166 correspond to respective holes that extend through the substrate 22 of the test strip 50.

Figure 14C:
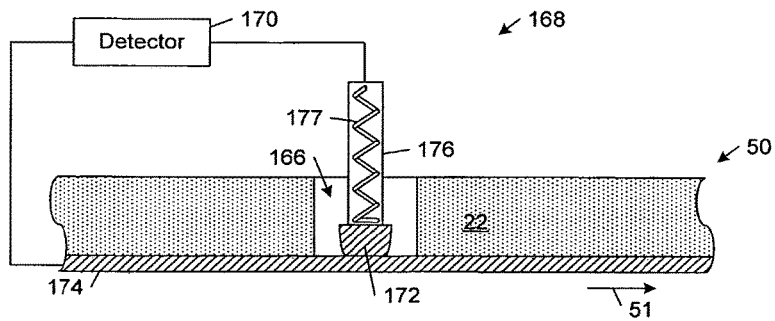
FIG. 14C is a diagrammatic view of the detection system on a different portion of the test strip shown in FIG. 14B.

In operation, at least one of the detection system 168 and the test strip 50 is moved relative to the other in a direction parallel to the lateral flow direction 51. The first electrical conductor 172 slides over the top surface of the test strip 50, which is supported by the second electrical conductor 174. The first electrical conductor 172 is urged by a spring 177 against the top surface of the test strip 50. In the position shown in FIG. 14B, the first and second electrical conductors 172, 174 are connected only by the high resistance material of the test strip 50. In this position, the detector 170 is configured to determine that there is an open circuit between the first and second electrical conductors 172, 174. In the position shown in FIG. 14C, on the other hand, the first electrical conductor 172 extends through the mechanical position marker 166 and directly contacts the second electrical conductor 174. In this position, the detector 170 is configured to determine that there is a closed circuit between the first and second electrical conductors 172, 174.

The detector 170 may determine whether there is an open circuit or a closed circuit between the first and second electrical conductors 172, 174 by comparing an electrical measurement (e.g., current, voltage, or resistance) between the first and second electrical conductors 172, 174 to a threshold value. For example, the detector may determine that there is an open circuit between the first and second electrical conductors 172, 174 when the measured electrical resistance value is greater than or equal to a threshold resistance value and that there is a closed circuit between the first and second electrical conductors 172, 174 when the measured electrical resistance value is below the threshold value.

In the embodiment shown in FIG. 14A, the mechanical position markers 160-166 are aligned with the upstream and downstream edges of the test region 16 and the control region 18 along the lateral flow direction 51. In this way, the data analyzer 46 readily may determine that the test and control regions 16, 18 are located between the detected positions of the mechanical position markers 160, 162 and 164, 166, respectively.

In other embodiments, the mechanical position markers may encode position information in different ways. For example, in some embodiments, the mechanical position markers may be positioned at regularly spaced locations along the edge of the test strip 50. As a result, the electrical measurements that are obtained near the edge of the test strip 50 vary in value in accordance with the pattern of the mechanical position markers. In this way, the mechanical position markers encode positions along the test strip 50 in the lateral flow direction 51. With respect to these embodiments, the data analyzer 46 may determine the encoded positions along the lateral flow direction 51 by incrementing a position counter with each measurement variation cycle (e.g., peak-to-valley) in the electrical measurements obtained from the edge of the detection zone 15.

In other embodiments, the first and second electrical conductors 172, 174 of the detection system 168 are replaced by a mechanical transducer (e.g., a stylus connected to a piezoelectric element) is dragged across the top surface of the test strip. In particular, the mechanical transducer generates signals corresponding to its movement in a direction normal to the surface of the test strip. The vertical motion of the stylus compresses the piezoelectric element, which generates a voltage response that varies linearly with the movement of the stylus. These signals indicate the surface profile variations across the surface of the test strip 50. With respect to these embodiments, the mechanical position markers may be implemented by holes, notches, dimples, or bumps on the top surface of the test strip 50.

III. Calibration Regions on a Test Strip and Reading Same

A. Overview

In some embodiments, one or more of the reference features on the test strip 50 are calibration regions that provide a reference optical response that may be used by embodiments of the diagnostic test system 10 to calibrate one or more components of a diagnostic test system and the assay measurements obtained by such a system and, thereby, increase the accuracy of the lateral flow assay results.

In general, the calibration regions may be laid out in the detection zone 15 of the test strip 50 in any of a wide variety of ways. In some implementations, the calibration regions are positioned near the regions of interest in order to reduce the effects of temperature or manufacturing variations across the test strip 50. In some of these implementations, the calibration regions are laid out adjacent to one or more of the regions of interest in the detection zone 15 of the test strip 50. For example, in one exemplary embodiment, the calibration regions may be laid out in the same way as the optical position markers 102-108 in the implementation shown in FIG. 10 or the same way as the optical position markers 118-124 in the implementation shown in FIG. 11.

In implementations of the test strip 50 that include a test region and one or more additional capture regions (e.g., another test region or a control region), one or more the additional capture regions may serve as a calibration region for calibrating one or more components of a diagnostic test system and/or calibrating the assay measurements obtained from the test region.

B. Measurement Calibration Regions

Figure 15:
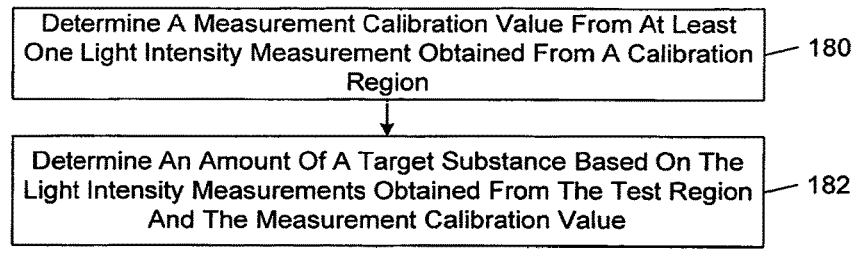
FIG. 15 is a flow diagram of an embodiment of a method of calibrating light intensity measurements that are obtained from a region of interest.

In some embodiments, the calibration regions are calibrated to provide a reference optical response that may be used by the data analyzer 46 to calibrate the light intensity measurements that are obtained from the regions of interest. FIG. 15 shows an embodiment of a method by which the diagnostic test system 10 calibrates the light intensity measurements that are obtained from a region of interest.

In accordance with this method, the data analyzer 46 determines a measurement calibration value from at least one light intensity measurement that is obtained from a calibration region (FIG. 15, block 180). The measurement calibration value may correspond to a statistical measure (e.g., a peak intensity value or average intensity value) that is computed from the light intensity measurements that are obtained from the calibration region.

The data analyzer 46 then determines an amount of a target substance (e.g., the target analyte captured by the test region 16 or the label captured by the control region 18) based on the light intensity measurements that are obtained from the region of interest and the determined measurement calibration value (FIG. 15, block 182).

In some implementations, at least one calibration region contains a calibrated amount of the test label 32 such that the optical response (e.g., reflected light intensity or fluorescent emission intensity) of the calibration region corresponds to a known quantity (e.g., number or density) of the test label 32. The data analyzer 46 may then scale the optical responses from the test region 16 and the control region 18 based on the optical response of the calibration region to obtain measures of the quantity of the analyte captured by the test region 16 or the quantity of the label captured by the control region 18.

In some implementations, the test strip 50 includes multiple calibration regions having different respective calibrated amounts of the same label. With respect to these implementations, the data analyzer 46 generates from the optical responses of the calibration regions a calibration curve mapping light intensities to measures of the quantities of the label. The data analyzer 46 may then map the light intensity measurements that are obtained from the regions of interest to a measure of the amount of a captured substance of interest (e.g., the target analyte captured in the test region 16 or the label captured by the control region 18).

In some implementations, the labeling zone 14 of the test strip 50 contains different colored labels that specifically bind to different respective analytes that may be present in the fluid sample. In these implementations, the test strip 50 may include one or more calibration regions that contain calibrated amounts of the different labels. In these implementations, the test strip 50 may include a separate calibration region for each label. Alternatively, the test strip 50 may contain one or more calibration regions each of which contains calibrated amounts of multiple different labels. The calibrated amounts of the different labels may be intermixed and distributed across the same calibration region or they may be located within different respective sub-areas of the same calibration region.

C. Detection Calibration Regions

In some embodiments, the calibration regions provide a reference optical response that may be used by the data analyzer 46 to calibrate one or more operational parameters of the detection system of the reader 44.

In this regard, the data analyzer 46 may optimize the wavelength characteristics of the components of the detection system that distinguish among the different light colors that are emitted by different labels on the test strip 50. For example, the data analyzer 46 may generate a signal that adjusts the wavelength passband of a tunable optical filter of the detection system to maximize the detected intensity of light received from a calibration region.

The data analyzer 46 also may adjust (e.g., normalize) the response of the detection system for the characteristic wavelengths of light received from the calibration regions. For example, the data analyzer 46 may generate a signal that adjusts the response of the detection system so that it produces a predetermined output value (e.g., a predetermined current value or a predetermined voltage value) in response to light obtained from the calibration region. The data analyzer 46 may generate a respective response adjustment signal for each wavelength range of interest (e.g., for the characteristic wavelength of each label carried by the test strip 50).

D. Illumination Calibration Regions

In some embodiments, the calibration regions provide a reference optical response that may be used by the data analyzer 46 to calibrate one or more operational parameters of the illumination system of the reader 44.

Figure 16:
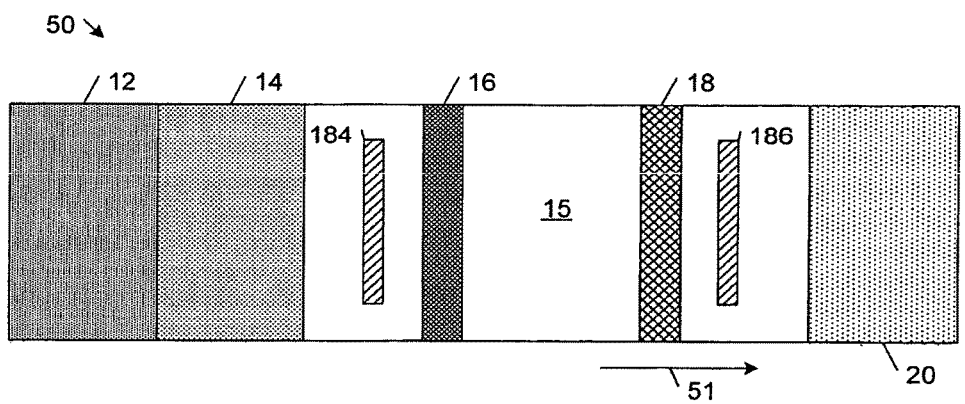
FIG. 16 is a diagrammatic view of an implementation of the diagnostic test system shown in FIG. 3.

FIG. 16 shows an embodiment of the test strip 50 that includes first and second illumination source calibration regions 184, 186. Each of the first and second illumination source calibration regions 184, 186 has a reflection or emission that is greater than the adjacent surface regions of the test strip with respect to light within a target wavelength range. In some implementations, the first and second illumination source calibration regions 184, 186 have reflectivities that are greater than 90% with respect to light within the visible wavelength range (i.e., 390 nm to 770 nm). In these implementations, the first and second illumination source calibration regions 184, 186 are formed of thin films of a metal (e.g., aluminum or gold). In other implementations, the first and second illumination source calibration regions 184, 186 include immobilized fluorescent particles (e.g., quantum dots) with secondary fluorescent emissions that may be used to calibrate one or more operational parameters of the illumination system of the reader 44.

Figure 17:
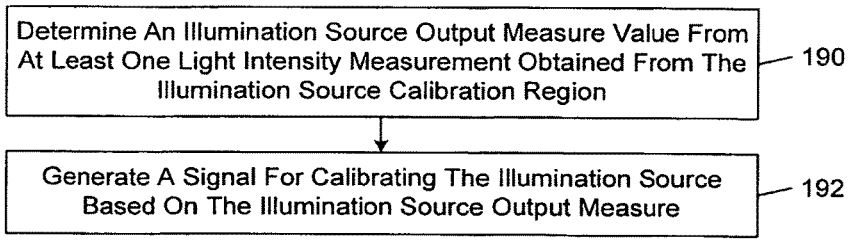
FIG. 17 is a flow diagram of an embodiment of a method of calibrating an illumination source of a diagnostic test system.

FIG. 17 shows an embodiment of a method by which the data analyzer 46 calibrates an illumination source of the reader 44.

In accordance with this method, the data analyzer 46 determines an illumination source output measure from at least one light intensity measurement obtained from the illumination source calibration region (FIG. 17, block 190). In some implementations, the illumination source calibration source corresponds to a statistical measure (e.g., a peak intensity value or average intensity value) that is computed from the light intensity measurements that are obtained from the illumination source calibration region.

The data analyzer 46 generates a signal for calibrating the illumination source based on the illumination source output measure (FIG. 17, block 192). In some implementations, the data analyzer 46 compares the illumination source output measure to a reference value. The data analyzer 46 may generate a control signal that increases the light intensity output of the illumination source when the illumination source output measure is below the reference value and decreases the light intensity output of the illumination source when the illumination source output measure is above the reference value. In some implementations, the data analyzer 46 may iteratively determine the illumination source output measure and generate the illumination control signal until the illumination source output measure is within a specified range of the reference value.

In the embodiment shown in FIG. 16, the first illumination source calibration region 184 is located upstream of the test region 16 and the second illumination source calibration region 186 is located downstream of the control region 18. In this way, the data analyzer 46 may detect variations in the output of the illumination source across the detection zone 15. In some implementations, the data analyzer 46 may scale the light intensity measurements obtained for the regions of interest based on the differences between the illumination source output measures determined for the first and second illumination source calibration regions 184, 186. The amount by which the light intensity measurements are scaled may be determined empirically and stored in a lookup table or represented by a parametric curve or some other function of the illumination source output measures.

IV. Conclusion

The embodiments that are described above provide lateral flow assay test strips that have one or more reference features. In some embodiments, the reference features are position markers that are aligned with respect to regions of interest in the test strip and may be used by embodiments of the diagnostic test system to identify light intensity measurements obtained from regions of interest. In some embodiments, the reference features are calibration regions that provide a reference optical response that may be used by embodiments of the diagnostic test system to calibrate one or more components of a diagnostic test system and the assay measurements obtained by such a system. In these ways, the embodiments described above improve the accuracy and precision with which analytes in a fluid sample may be assayed.

Other embodiments are within the scope of the claims.

For example, the embodiments are described above in connection with an implementation of the diagnostic test system 10 that includes a two-dimensional array of light detectors 70. These embodiments also may be integrated with different implementations of the diagnostic test system 10, including implementations in which the reader 44 includes a one-dimensional array of light detectors and a mechanism for imparting relative motion between the optical inspection components of the reader and the test strip-.

Some implementations of the test strip 50 may include two or more of the different types of reference features that are described above.

In the embodiments described above, the test regions, control regions, calibration regions, and position markers are shown as having rectangular shapes in the plane of the detection zone 15. In general, however, these features may have any type of shape, including a polygonal (e.g., rectangular) shape and a curved (e.g., elliptical or circular) shape.

What is claimed is:

1. A diagnostic test system, comprising:
   a test strip that comprises a flow path for a fluid sample, a sample receiving zone coupled to the flow path, a label that specifically binds a target analyte, a detection zone coupled to the flow path and comprising a test region exposed for optical inspection and having an immobilized test reagent that specifically binds the target analyte, and at least one reference feature comprising an illumination source calibration region;
   a reader comprising an illumination source operable to illuminate the test strip when the test strip is loaded in a port for receiving the test strip, the reader further comprising a detection system that is configured to obtain light intensity measurements from exposed regions of the test strip when the test strip is loaded in the port; and
   a data analyzer comprising software configured to
      process the light intensity measurements obtained by the reader,
      determine an illumination source output measure from at least one light intensity measurement obtained from the illumination source calibration region,
      generate a control signal calibrating the illumination source based on a comparison of the determined illumination source output measure to a reference value, and
      adjust a light intensity output of the illumination source when the determined illumination source output measure is different than the reference value.

2. The system of claim 1, wherein the control signal is configured to calibrate one or more operational parameters of the illumination source based on at least one light intensity measurement obtained from the illumination source calibration region.

3. The system of claim 1, wherein the at least one reference feature comprises a first illumination source calibration region and a second illumination source calibration region.

4. The system of claim 3, wherein the first illumination source calibration region and the second illumination source calibration region have a reflection or an emission that is greater than a reflection or an emission of an adjacent region of the test strip with respect to light within a target wavelength range.

5. The system of claim 3, wherein the first illumination source calibration region and the second illumination source calibration region reflect greater than 90% of light within a target wavelength range of about 390 nm to about 770 nm.

6. The system of claim 3, wherein the first illumination source calibration region and the second illumination source calibration region comprise a film of metal.

7. The system of claim 3, wherein the first illumination source calibration region and the second illumination source calibration region comprise immobilized fluorescent particles.

8. The system of claim 3, wherein the first illumination source calibration region and the second illumination source calibration region comprise a different surface profiles on the test strip than adjacent areas of the test strip.

9. The system of claim 1, wherein the illumination source output measure comprises a peak intensity value or an average intensity value computed from the at least one light intensity measurement.

10. The system of claim 1, wherein the data analyzer comprises software configured to generate the control signal based on the determined illumination source output measure.

11. The system of claim 1, wherein the data analyzer comprises software configured to increase the light intensity output of the illumination source when the determined illumination source output measure is less than the reference value.

12. The system of claim 1, wherein the data analyzer comprises software configured to decrease the light intensity output of the illumination source when the determined illumination source output measure is greater than the reference value.

13. The system of claim 1, wherein the data analyzer comprises software that is configured to iteratively generate control signals until the determined illumination source output measure is within a specified range of the reference value.

14. The system of claim 3, wherein the first illumination source calibration region is located upstream of the test region and the second illumination source calibration region is located downstream of the test region, and wherein the data analyzer comprises software configured to determine a first illumination source output measure from at least one light intensity measurement obtained from the first illumination source calibration region and a second illumination output measure from at least one light intensity measurement obtained from the second illumination source calibration region.

15. The system of claim 14, wherein the first illumination source output measure is different than the second illumination source output measure.

16. The system of claim 15, wherein the data analyzer comprises software configured to detect variations in the output of the illumination source across the detection zone based on the difference between the first illumination source output measure and the second illumination source output measure.

17. The system of claim 15, wherein the data analyzer comprises software configured to scale light intensity measurements obtained from the test region and a control region based on the difference between the first illumination source output measure and the second illumination source output measure.

18. The system of claim 17, wherein the amount the data analyzer scales the light intensity measurements is obtained from a lookup table or a parametric curve.

\* \* \* \* \*